United States Patent [19]

Liebert

[11] 4,189,616
[45] Feb. 19, 1980

[54] MAXIMUM UTILIZATION OF ENERGY IN ISOPARAFFIN RECYCLE IN ALKYLATION

[75] Inventor: Timothy C. Liebert, Houston, Tex.

[73] Assignee: Phillips Petroleum Company, Bartlesville, Okla.

[21] Appl. No.: 874,591

[22] Filed: Feb. 2, 1978

[51] Int. Cl.$^2$ ............................................. C07C 3/50
[52] U.S. Cl. ....................................... 585/701; 203/1; 203/25; 208/365; 208/DIG. 1
[58] Field of Search ........... 260/683.4, 683.43, 683.48, 260/683.62; 202/160; 208/365, DIG. 1, 353, 356; 203/1

[56] References Cited

U.S. PATENT DOCUMENTS

| | | | |
|---|---|---|---|
| 2,990,437 | 6/1961 | Berger | 260/683.43 |
| 3,115,445 | 12/1963 | Kleiss et al. | 208/DIG. 1 |
| 3,187,066 | 6/1965 | Nathan | 260/683.62 |
| 3,215,752 | 11/1965 | Vermilion, Jr. | 260/683.48 |
| 3,676,304 | 7/1972 | Hobbs et al. | 202/160 |
| 3,763,022 | 10/1973 | Chapman | 260/683.4 |
| 3,857,904 | 12/1974 | Chapman | 260/683.48 |
| 3,939,045 | 2/1976 | Walker | 208/DIG. 1 |

Primary Examiner—George Crasanakis

[57] ABSTRACT

In a fractionation system wherein a stream of heat-containing fluid is taken from a zone effecting at least a partial control of at least one operating condition in said zone by withdrawing said fluid at a rate responsive to and correlated with a change in said condition and utilizing the heat in said withdrawn fluid.

In one application, in operation of an HF alkylation of isoparaffin with olefin, in which a mixed paraffins feed is fractionated in a first fractionator to obtain isoparaffin therefrom, an alkylate product is fractionated in a second fractionator to recover isoparaffin as a side draw from the second fractionator the temperature in the upper section of the second fractionator is controlled by removing more or less isoparaffin vapor therefrom, determining the change in amount of isoparaffin being removed and applying this measurement to adjust the amount of isoparaffin fed to the mixed paraffins feed fractionator reboiler section, increasing isoparaffin to said section when the preselected temperature in the overhead outlet of the alkylate product fractionator attempts to increase (and vice versa) and causing adjustment in the amount of steam needed to supply the remainder of heat required to reboil the mixed paraffins fractionation zone. In one embodiment the isoparaffin vapor removed from the alkylate product fractionator is passed through a cooling zone, condensed therein, and the flow of the produced condensate, while being passed to the alkylation, is detected and is representative of the attempted temperature change in the alkylate product fractionator and is employed to adjust flow of the isoparaffin vapor to the isoparaffin vapor-heated reboiler in the mixed paraffin fractionation zone; the operation providing for suitable adjustment of steam to the steam reboiler to said mixed paraffins fractionation zone. In another modification, the amount of steam is further controlled with respect to the amount of total heat needed in the reboiled section of the mixed paraffins fractionation zone in manner correlated with the composition of paraffins removed in a side draw from said mixed paraffins fractionation zone.

17 Claims, 1 Drawing Figure

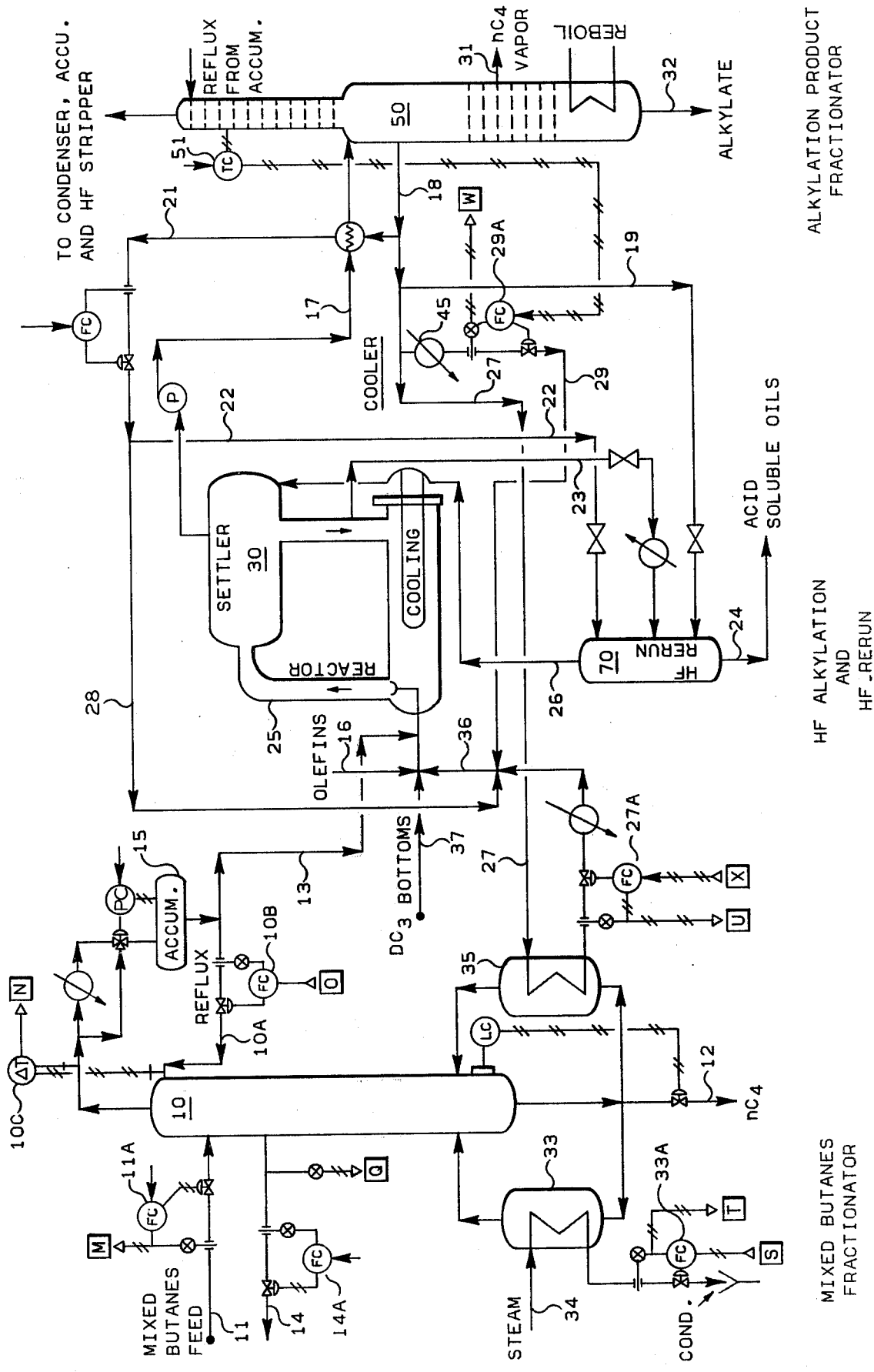

MAXIMUM UTILIZATION OF ENERGY IN ISOPARAFFIN RECYCLE IN ALKYLATION

This invention relates to the alkylation of an isoparaffin with an olefin to produce an alkylate. In one of its aspects the invention relates to the alkylation of an isoparaffin with an olefin in the presence of HF acid. In a more specific aspect, the invention relates to the utilization of heat available in a heat-containing fluid, e.g., in a vaporous hydrocarbon, e.g., isobutane being removed from an alkylate product fractionation zone.

For sake of brevity the invention will be described in terms of "isobutane". It will be understood by one skilled in the art in possession of this disclosure having studied the same that the invention in its essential concepts is applicable to other than "isobutane", e.g., to other isoparaffins, paraffins, or related or other hydrocarbons or materials which are extant in an overall operation as herein described.

Broadly, the invention, in one of its basic concepts, in a fractionation system wherein a stream of heat-containing fluid is taken from a zone, effects at least a partial control of at least one operating condition in said zone by taking said fluid from said zone responsive to and correlated with a change in said condition and utilizes the heat in said fluid so obtained.

To facilitate the understanding of that which follows reference is now made to U.S. Pat. No. 3,763,022, issued Oct. 2, 1973 to Charles C. Chapman, the disclosure of which is incorporated herein by reference.

In the patent drawing there is shown an alkylation product fractionator and a mixed butanes fractionator, towers 12 and 21, respectively. Isobutane vapor stream 19 taken from tower 12 is passed to tower 21 in indirect heat exchange reboiler 20 thus making use of heat content of the isobutane vapor. Tower 21 is equipped with a steam reboiler 27 to which steam is fed controlled by a flow controller which is reset by temperature controller 28 responsive to the temperature in the lower portion of the tower (21). There are also removed from tower 12 an overhead propane stream 15, a liquid isobutane stream 16, a vaporous normal butane stream 17 and the usual alkylate stream 18. Tower 12 is refluxed with condensed overhead 14 which is described in the patent as being propane.

In one of its specific concepts, the present invention provides a method for removing maximum heat from vaporous isobutane passing from the alkylation product fractionator to the mixed butanes fractionator hot isobutane-heated reboiler, thereby minimizing as far as possible the amount of steam used to supply the additional heat needed to operate the mixed butanes fractionator, the removal of said heat being accomplished by controlling the alkylation product fractionator upper portion preset temperature by removing responsive to said temperature more or less vaporous isobutane as a side stream as said temperature tends to rise or fall, respectively, and passing, correspondingly, more or less hot isobutane vapor to the isobutane-heater reboiler in the lower zone of the mixed butanes fractionator.

In another of its specific concepts, the invention provides a method wherein hot isobutane vapors are cooled, condensed, and passed by flow-controlled operation to the alkylation reaction, the rate of flow being adjusted responsive to variation in temperature in the top portion of the alkylation product fractionation zone from which said vapors are withdrawn, the change in rate of flow being detected and employed to adjust the rate of flow of hot isobutane vapors also flowing from said alkylation product fractionator to the hot isobutane-heated reboiler in the mixed butanes fractionator, involving passing more isobutane vapor to the reboiler when the temperature is tending to rise in the alkylation product fractionator, and vice versa.

In a further specific concept of the invention it provides a method as herein described wherein the isobutane vapors from the alkylation product fractionation zone are passed in part into indirect heat exchange with alkylation effluent being passed to said alkylation product fractionation zone, in part to the cooling and condensing, earlier described, and in major part—in maximized part—to said reboiler. In a further concept, still, the invention provides determining, as by creating a signal representative thereof, the temperature in the top portion of the alkylation product fractionation zone and responsive to such signal taking more or less hot isobutane vapor from said zone to said reboiler as said temperature tends to rise or fall, respectively.

In another of its specific concepts, the invention additionally takes a minor portion of the hot isobutane vapors wherewith to reboil an HF rerun operation and another portion of heat exchanged vapors, which are now cooler, and substantially condensed, to reflux said HF rerun operation.

In a further specific concept of the invention, the invention provides an operation in which the additional heat required for the mixed butanes fractionation zone reboiling, which is supplied by steam, is supplied by steam in a quantity determined by giving consideration to the composition of hydrocarbon in the reboiler portion of said mixed butanes fractionation zone, as measured in a hydrocarbon side draw taken from a locus above the reboiler and below the feed, as by producing signals representative of the feed to said zone and of the several streams emanating from said zone, correlating these signals, etc.

In one embodiment of the invention, to be further described, signals are fed to a computer which is programmed to virtually instantly produce commanding signals to control the flows which are extant in the operation.

It is an object of this invention to save heat in a heat-containing fluid obtained in a fractionation and to maximize the heat thus saved.

It is a further object of this invention to provide an improved process for the alkylation of hydrocarbons. It is another object of the invention to provide an improved process for the alkylation of an isoparaffin with an olefin, e.g., alkylation of isobutane and olefin or olefins such as propylene and/or butylenes in the presence of HF alkylation catalyst. It is a further object of the invention to provide a modus operandi for such alkylation in which the heat recovered from a hot isobutane vapor stream is maximized while minimizing thusly additional heat required to be furnished, as by steam, for the fractionation of a mixed butanes feed to the process, which feed contains the desired isobutane along with normal butane. Another object of the invention is to provide a method for the control of an alkylation product fractionator. Still a further object of the invention is to provide in relation to the control of an alkylation product fractionator a control system wherewith to maximize the amount of hot isobutane vapor passed from said fractionator to a reboiler in the overall operation. It is a further object still to provide a combination of steps in a method wherewith to maximize utilization of heat in hot isobutane vapors taken from an alkylation product fractionator while minimizing the amount of steam required for the reboiling of a mixed butanes fractionation by determining the actual Btu or heat requirement fo reboiling the same. Another object of the invention is to provide a new method of operation HF alkylation wherein an isoparaffin is alkylated with an olefin in which the Btu or heating requirement as well as cooling medium requirement are minimized by providing to a center of determination and operation, e.g., a computer, certain data derived from the ongoing operation and in said center determining information or signals required to be relayed to various portions of the operation, e.g., to steps therein to conduct the same with utmost of efficiency and economy.

Other aspects, concepts, objects and the several advantages of the inventon are apparent from a study of this disclosure and the appended claims.

According to the invention a fractionation zone is operated to control an operating condition therein by removing therefrom a heat-containing fluid responsive to and correlated with a change in said condition and utilizing the heat in the removed fluid.

According to the invention, in a specific definition thereof, in a process for the alkylation of an isoparaffin with an olefin, as herein described, an alkylation product fractionator or fractionation zone is operated to separate a light hydrocarbon, e.g., propane, overhead, an isoparaffin, e.g., isobutane vapor sidestream, a normal paraffin, e.g., normal butane vapor sidestream, and an alkylate gasoline product bottoms; the fractionator being reboiled and being fed, after heat exchange with one portion of removed hot isobutane vapor, the fractionation feed from an HF alkylation reaction settler, i.e., the hydrocarbon phase from said settler, the fractionator being refluxed while the temperature of the fractionator upper portion is controlled at a preselected value by removing more or less hot isobutane vapor therefrom as the temperature tends to rise or fall at said top portion in said fractionator, respectively.

Also, according to the invention, another portion of the hot isobutane vapor from said fractionator is cooled, condensed and returned to the alkylation, the flow rate of the returned stream being measured and controlled responsive to said top portion temperature and as flow rate tends to increase, increasing the flow of still another portion of hot isobutane vapor to the reboiler of the mixed butanes fractionator, and vice versa.

Further according to the invention, the flow rate of the cooled, condensed isobutane, last mentioned, is determined and the determination or signal representative thereof is employed to determine the flow rate of hot isobutane vapor to said reboiler directly from said alkylation product fractionator.

Still further according to the invention determinations and/or signals are correlated, preferably with still other determinations and/or signals in the overall operation to control the amount of steam or rate of flow thereof to the reboiler of the mixed butanes fractionator, such other determinations being signals being obtained from the hot isobutane reboiler and from streams entering and leaving said mixed butanes fractionator including, importantly, the amount of steam entering and/or being required by said steam reboiler on said mixed butanes fractionator.

Variation and modification are possible within the scope of the invention as described herein. One skilled in the art in possession of this disclosure having studied the same will understand that various engineering details of operation are necessarily omitted for sake of simplicity. Thus, certain pumps, valves, control instruments, surge drums, etc., are not included. Herein and in the claims "operating condition" is intended to include temperature, pressure and composition.

The drawing illustrates diagrammatically an operation according to the concept or concepts of the present invention.

Generally, the drawing shows from left to right a mixed butanes feed fractionator 10 and HF alkylation operation involving a reactor 25 and a settler 30 and an alkylation product fractionator 50.

According to the invention, the temperature of the top portion of tower 50 is controlled by removing more or less hot isobutane vapor by 18 and passing the same by 27 to reboiler 35. While such flow is being practiced, other flows are being maintained and/or regulated.

It will be noted that in the Chapman patent, above referred to and incorporated herein by reference, there is removed from the top of alkylation product fractionator 12 a liquid isobutane stream as well as a vaporous isobutane stream by pipes 16 and 19, respectively.

According to the present invention, as stated, the tower top temperature is controlled by removal of more or less hot isobutane at 18 responsive to the temperature in the top portion of tower 50.

Further referring to the Chapman patent, the vaporous isobutane stream 19 is passed directly to reboiler 20 in the mixed butanes fractionator 21 of the patent.

Referring to the drawing of this application, isobutane stream 18 is divided into at least the following streams: stream 21, which is heat interchanged with the incoming feed to the fractionator, pumped from settler 30 by 17; stream 19 used to reboil an HF rerun tower 70; a relatively small flow stream which is cooled and condensed at 45 and passed by 29 and 36 to the alkylation reactor 25 together with olefins introduced at 16; and by 27 directly to the reboiler 35 of the fractionator 10. In addition, the isobutane-containing stream from a depropanizer (not shown) bottoms is added by 37 to alkylation 25.

According to the invention, the flow in 27 is maximized by at least detecting the flow through the flow controlled valve in 29, the control of the flow being responsive to the temperature in top portion of the tower 50, on TRC 51. Whenever temperature in the top of tower 50 tends to increase the flow controller will open the valve in 29 drawing more hot vapors through the cooler thus increasing the flow of hot vapors from the tower. However, according to the invention, the flow in 29 is determined and in a preferred form is caused to produce a signal which is then employed to regulate the withdrawal of produced condensate from reboiler 35, the flow of condensate from the reboiler being immediately increased thus to maximize hot isobutane vapor flowing from tower 50 to reboiler 35. Conversely, if the temperature in the top portion of tower 50 is tending to decrease, the flow through 29 will be decreased and the corresponding determination or signal obtained from the flow in 29 will be employed or directed to regulate and to cut down the flow of condensate from reboiler 35.

In lieu of cooling and condensing at 45 to produce a measurable rate of flow of liquid so that changes in rate of its flow can be measured to produce an indication or signal, other means of creating a measurable rate of flow change responsive to tendency of the tower 50 top portion temperature to change can be employed. In practice, any means of controlling the flow of hot isobutane vapor to reboil tower 10 can be used. Thus, any indication generated by tendency of the temperature of tower 50 to change can be transduced by any known means to increase or to decrease the flow of hot isobutane vapor to reboil tower 10. Thus, as an equivalent method or means of maximizing flow of hot isobutane vapor from 50 to reboil 10, in lieu of a temperature change detection, tendency to change composition of the overhead from 50 can be used to control the vapor flow.

Still according to the invention, there are provided means to determine and/or to produce signals representative of determinations made on the overhead from tower 10, on the mixed butanes feed 11 to the tower, on a hydrocarbon sidestream 14 which may be withdrawn from isomerization of normal butane therein to isobutane, and also on the stream condensate from the steam reboiler 33 feed steam at 34. For sake of completeness, tower 10 bottoms, constituting essentially normal butane, are removed at 12 the valve in which is on liquid level control to maintain a suitable liquid level in the bottom of tower 10 which is, as stated, being reboiled.

By way of further illustration of the invention and its several inventive concepts taken singly or in combination the following description is now given including additional operational details and some reference to signals which, preferably, are referred to a suitably programmed computer.

The programming of a suitable computer is well within the skill of the art of programming computers. Apart from the execution of the inventive concepts here set forth and described, the actual detailed operation of the computer does not form any basic part of the invention. It will be understood by those skilled in the art in possession of this disclosure having studied the same that all of the determinations herein referred to or which are made in the operation or process and which may be computerized can be made by persons and employed by persons to effectuate the operation.

Again referring to the drawing, a mixture comprising isobutane and normal butane, from any source such as butane isomerization, refinery mixed butanes, etc., is passed on FRC 11a to mixed butanes fractionator 10 by 11. More than one stream of mixed butanes can be charged to unit 10, each at a different feed tray, the tray being selected depending on the composition of the feed being added to that tray and the composition on that tray. A bottoms stream yield rich in normal butane is recovered at 12. The overhead vapor comprising isobutane, it being desired to maximize recovery of isobutane for feed to alkylation by 13, from unit 10 is condensed and passed to accumulator 15, with a portion of the produced liquid refluxing unit 10 via 10a on flow control 10b. A yield stream 13, comprised of a major portion of isobutane, is charged to subsequent HF alkylation. A side stream comprising isobutane and normal butane is removed from unit 10 on flow control 14a by 14 and it can be and preferably is passed to butane isomerization to produce additional isobutane for the system.

Unit 10 is reboiled by two indirect heat exchangers, 33 and 35. In accordance with a basic concept of the invention, steam 34 is used at a minimum quantity in exchanger 33, while maximum hot isobutane vapor 27, from a source later described, is used in exchanger 35 to reboil unit 10.

Thus, as earlier noted, the maximum possible heat to reboil unit 10 is taken from vapor stream 27 which results from fractionation to recover alkylate, later described. Stream 27 has to be cooled and condensed before being passed to alkylation.

Recycled isobutane 28, feed isobutane 13, olefin feed 16 and additional recycle isobutane 36 are charged to HF alkylation riser reactor 25 wherein, in the presence of liquid HF catalyst, isobutane is alkylated with the olefin feed to produce high octane alkylate gasoline containing components. U.S. Pat. No. 3,213,157, issued Oct. 19, 1965, to Phillips Petroleum Company, details such an HF alkylation operation. The mass from reactor 25 is passed to phase settler 30 wherefrom the lower liquid, HF, is recycled after indirect cooling to reactor 25.

A portion of the system HF acid is charged by 23 and heating means to HF rerun column 70. Liquid isobutane 22 is used to reflux rerun column 70. Hot isobutane vapor 19 is used to strip HF from acid-soluble oils which are removed by 24. The isobutane vapor-HF overhead 26 is passed from rerun 70 back to alkylation, e.g., to the settler 30.

The supernatant separated liquid hydrocarbon phase from HF alkylation settler 30 is passed by 17, indirectly heated with a portion 21 of hot isobutane vapors and charged to alkylation product fractionator 50. Overhead from unit 50 comprises HF and propane and is passed via condensing (not shown) to an accumulator wherefrom recovered HF is returned to the alkylation. A portion of the liquid hydrocarbon, substantially propane, is used to reflux unit 50. The yield portion of propane preferably is passed to an HF stripper. Overhead from this stripper is condensed and passed to said accumulator. Bottoms from this stripper are recovered as liquid propane, which may be treated for fluoride removal, e.g., AlF$_3$, solid KOH, NaOH solution, and the like. A side-draw of normal butane vapor 31 can be removed from unit 50. Alkylate product (pentanes and heavier) is removed at 32.

A hot isobutane vapor side-draw 18 from unit 50 is utilized in many ways, but with maximizing of its use to reboil tower 10, according to the invention, whereby only minimum steam at 34 will be required.

A portion of isobutane vapor 18 is used via 21 in that amount required to preheat the hydrocarbon charged by 17 to unit 50. A portion of now-condensed isobutane in 21 is passed by 22 to reflux HF rerun unit 70 and the remaining major portion 28 is recycled to alklyation reactor 25. A portion of isobutane vapor 18 is passed by 19 to reboil HF rerun unit 70.

When the temperature just below the reflux tower 50 tends to rise above a preset value, the valve on flow control 29a in conduit 29, allowing flow of isobutane vapor through condenser 45, is further opened in response to a signal to control 29a from the temperature controller 51 at top of tower 50. This additional removal of isobutane vapor, withdrawn from tower 50 via 18, decreases the heat going up the tower, and thus maintains the preset temperature in the upper part of tower 50. As the flow of isobutane vapor from the tower 50 passes through conduit 29, a flow signal "W", sent to the computer, effects the further opening of the valve 27a in the isobutane condensate removal line on reboiler 35, so that more flow of isobutane vapor passes via 27 to reboiler 35, as desired. Computer signal "X" controls via flow control 29a this opening of valve 27a on the isobutane flow through reboiler 35. Signal "S"

from the computer activates control 33a on the valve on the steam condensate from reboiler 33 to minimize even further the steam or "outside" heat required in reboiler 33. As the temperature in the top of tower 50 is thusly maintained (by rate of removal of isobutane vapor 18 from tower 50), the signal from the temperature controller 51 effects via flow control 29a a closing down on the flow of isobutane vapor passed to the water-cooled condenser 45. Ultimately, a steady state operation occurs with maximizing of the flow of isobutane vapor to reboiler 35 (and minimizing, even to zero, flow thereof to water-cooled condenser 45).

Maximizing of isobutane vapor to reboiler 35 minimizes flow of steam to reboiler 33, according to the invention. Therefore, according to the invention, at least the temperature in the upper part of tower 50 controls and aids in maximizing the flow of isobutane vapor to reboiler 35.

The condensed isobutane is passed via cooling means as recycle isobutane 36 for the HF alkylation system. The operation utilizes maximum available heat contained, within the operation, in the hot isobutane vapor recovered from unit 50 via conduit 18.

Also, according to the invention, which can be hand operated as already described, an analog computer operation is established to use certain signals representing flow rates, compositions, differential temperature, etc., in the operation shown on the drawing, as at Q, N, M, T, U, X, O, etc., to better maximize the described use of hot isobutane vapor by 18 and 27 for heating reboiler 35, thus to minimize use of steam or "outside" heat in companion reboiler 33, and also to minimize flow in 29 through 45.

The following is given to more fully describe the computer aspect of the invention. The operation to be effected has been fully described herein. It is to be recognized that by stationing persons at each point in the operation at which a signal is generated and/or to which a signal is furnished, the persons working as a team would be acting in lieu of a computer.

ANALOG COMPUTER SYSTEM

Functions of System:
I Feed Forward Control:
  (a) Predict the total heat to reboilers 33 and 35 of column 10:
    (1) $a \cdot M$ = total predicted heat ($H_p$) required.
  (b) Predict Internal Reflux $R_I$ to column 10:
    (2) $R_I = C \cdot (H_p)$ $$O = \frac{d \cdot R_I}{[1 + \frac{C_p}{L}(N)]} \quad (3)$$

II Feedback Trimming of Total Heat Requirement to Control Isobutane Concentration in Stream 14:
  (4) Total Heat Required ($H_R$) = Total Heat Predicted ($H_p$) + Trimming Correction, where the trimming correction is a function of the error between "Q" and "$Q_o$". Where "Q" is the isobutane concentration signal and "$Q_o$" is the desired isobutane concentration in 14.
  (5) Trim Correction = $k \cdot (Q - Q_o)$ III Maintaining a Small (Near Minimum) Usage of Reboiler Steam 34 as Necessary for Control Purposes. (System Adjusts Flow of Isobutane Vapor 27 for Maximum Usage of Waste Heat):

$$S = \text{Total Heat Required } (H_R) - eU \quad (6)$$

Set point X on stream 27 flow controller is varied to hold flow at 29 constant; i.e.,
  (7) $dX/dt(\text{time}) = j \cdot (W - W_o)$, for proportional control.
  If $T < S_{min.}$, then $S = S_{min.}$, and $$X = (\text{Total Heat Required } (H_R) - f \cdot S_{min.})/e \quad (8)$$

SUMMARY OF LETTERS USED IN ANALOG COMPUTER CONTROL

M represents the mass rate of flow of feed butanes 11 to column 10; this signal M is transmitted to the analog computer;

a is a constant;
c is a constant;
d is a constant;

O represents the signal from the computer actuating control on the amount of reflux passed to column 10. O is the set point signal to internal reflux flow controller;

N represents the temperature difference between the overhead vapor of tower 10 and the reflux charged thereto. This signal N is transmitted to the computer;

$R_I$ is the internal reflux;

Cp is the value of the molar heat capacity (between column 10 overhead temperature and reflux temperature);

L is the heat of vaporization at the column 10 overhead vapor temperature;

Q is the signal representing the isobutane concentration in 14. This signal Q enters the computer;

Qo is the desired isobutane concentration in 14;

k is a constant;

S represents a signal which is the set point value for the steam reboiler 33 steam flow controller on 34 steam flow; S is a signal from the computer;

e is a constant;
f is a constant;
j is a constant;

U represents the actual (measured flow) rate of flow of insobutane vapor 27 to reboiler 35. This signal is transmitted to the computer;

T represents the actual (measured flow) rate of steam 34 through reboiler 33. This signal T is transmitted to the computer;

X represents a signal from the computer to adjust the set point on the flow controller to regulate the rate of flow of isobutane vapor to reboiler 35;

W represents the rate of flow of cooled and condensed isobutane vapor 29. This signal W is transmitted to the computer. This actual rate of flow in 29 is controlled in response to the temperature in the upper portion of tower 50;

$W_o$ is the desired flow of isobutane vapor through condenser 45 in line 29; and dX/dt is the change of the isobutane 27 flow controller set point X with respect to time.

Note that various square root means, transmitters, pressure/electric transducers, electric/pressure transducers, and the like are not shown on the drawing for sake of simplicity. One skilled in this art and in possession of this disclosure, and, having studied this disclosure, will be able to supply the various means above mentioned.

The employment of computer control to accomplish maximum use of heat contained in the isobutane vapor from tower 50 in reboiler 35 can be done variously as the computer-engineer-programmer will understand.

The concept of the present invention, which is a basic concept underlying the overall operation as described in the drawings and covered in the claims, in that maximum use of heat in the isobutane vapor from tower 50 to which that heat must be supplied in tower 50 shall be transferred to reboiler 35.

It will be evident to one skilled in the art having studied this disclosure that increased energy savings are made possible by improving the control system in which isobutane vapor side-draw from the main tower 10 is condensed or returned to the HF alkylation. Thus, while the condensing of a portion of isobutane is employed to create the signal by which the feed of hot isobutane vapor to the reboiler 35 is maximized, this stream is and can be kept at a minimum, there being other streams providing the necessary recycling of isobutane directly to the HF alkylation. As can be seen, the condensate from reboiler 35 is passed by 36 to the alkylation even as are ultimately all other isobutane stream or streams which may contain some isobutane.

Normally, as in prior methods, the propane and some isobutane in the overhead from tower 50 is controlled by the isobutane recycle vapor side-draw flow rate which is reset by a temperature recorder controller (TRC) which seeks to maintain a constant temperature on the main tower top portion to produce the desired propane composition, usually with minimum isobutane therein. The isobutane side-draw flow controller is reset by the TRC and thus the TRC controls the isobutane flow rate to the water condenser 45. This flow rate is normally, in prior operations, set at about 15% of the total isobutane vapor side-draw from the tower 50. All other isobutane vapor side-draw flow rates are held constant. In particular, the flow recorder controller which controls the isobutane vapor flow rate to the mixed butanes fractionator reboiler 35 is held constant to keep the heat input to the mixed butanes fractionator as steady as possible.

In the invention, an analog computer is used to steady the operation of the mixed butanes splitter. This is done by holding the internal reflux constant, and manipulating the total heat input into the column to hold the isobutane content in the mixed butanes fractionator side-draw to a low value. The total heat content to the mixed butanes fractionator is calculated by multiplying the heat of condensation of steam and isobutane by their respective heats of condensation and summing. As the heat input to the column is manipulated to meet the required isobutanes specification in the side-draw, the total heat content is manipulated by adjusting the flows of steam and isobutane by the procedure which minimizes the steam consumption.

To carry out the concept of this invention, to maximize utilization of the heat content of the isobutane recycled stream, the operation according to the invention has been conceived.

Thus, according to a specific concept of the invention, the control system is so operated that the set point on the flow controller of the mixed butanes splitter isobutane reboiler 35 is reset by a signal indicating the valve position on the motor valve which allows isobutane vapor recycle 29 to flow to water cooled condenser 45. As the isobutane water-cooled condenser valve is further opened to control the temperature at the top section of the main tower 50, i.e., to cool tower 50, the valve controlling the vapor isobutane 27 flow to the mixed butanes fractionator reboiler 35 is further opened, thus further increasing the flow of isobutane via 18 from tower 50. The net effect of this is that a signal from the temperature controller in the upper part of tower 50 will close down or caused to be closed down the isobutane water-cooled condenser valve in 29 at least to an extent. Ultimately, a steady operation is achieved when the flow of isobutane vapor 29 to the water condenser will be at a minimum, isobutane vapor 27 to reboiler 35 will be at a maximum, and steam consumption in reboiler 33 at the mixed butanes fractionator will be at a minimum.

One skilled in the art will recognize that the flow from the water-cooled condenser can be split range in order to adequately control the flow at a value much lower than the maximum designed flow. In one design operation the water-cooled condenser 45 is designed for a maximum flow of about 127,747 pounds per hour isobutane vapor recycle. Without split range control it would be necessary to control the flow at not less than 32,000 pounds per hour in order to achieve good control (4:1 ratio). By using a split range control system, the flow of isobutane vapor recycle to the water-cooled condenser 45 can be held as low as 6,400 pounds per hour, which amounts to a considerable additional savings in energy.

To still further illustrate the operation of the invention, the following calculated operating conditions are given:

OPERATING CONDITIONS

| (10) Mixed Butanes Fractionator: | |
|---|---|
| Temperature, °F.: | |
| Top | 119 |
| Bottom | 149 |
| Pressure, PSIA., | 100 |

| (15) Unit 10's Accumulator: | |
|---|---|
| Temperature, °F. | 104 |
| Pressure, PSIA., | 85 |

| (50) Alkylation Product Fractionator: | |
|---|---|
| Temperature, °F.: | |
| Top | 156 |
| Bottom | 423 |
| Pressure, PSIA: | |
| Top | 225 |
| Bottom | 230 |

| Unit (50) Overhead Accum. (Not Shown): | |
|---|---|
| Temperature, °F. | 120 |
| Pressure, PSIA., | 210 |

| (45) Condenser: | |
|---|---|
| Isobutane in, °F. | 168 |
| Isobutane out, °F. | 100 |

Steam Rate (34), 10,500 lbs/hr. of 50 PSIG steam.

TYPICAL CALCULATED EXAMPLE (BARRELS/DAY)

| Component | 11 | 12 | 13 | 14 | 16 | 17[a] | 18 | 19 | 21 |
|---|---|---|---|---|---|---|---|---|---|
| HF | — | — | — | — | — | 1,135 | 256 | 2 | 35 |
| Ethane | 1 | — | 1 | — | 2 | 3 | — | — | — |
| Propylene | — | — | — | — | 5,837 | — | — | — | — |
| Propane | 597 | — | 597 | — | 2,308 | 18,111 | 14,200 | 115 | 1,924 |
| Isobutane | 11,142 | 688 | 9,873 | 581 | 5,063 | 141,525 | 131,712 | 1,064 | 17,852 |
| Butenes | — | — | — | — | 6,078 | — | — | — | — |
| n-Butane | 20,304 | 13,980 | 471 | 5,853 | 1,020 | 10,190 | 8,322 | 67 | 1,128 |
| Pentanes+ | 965 | 886 | — | 79 | 203 | 23,202 | 1,819 | 4 | 257 |
| Total | 33,009 | 15,554 | 10,942 | 6,513 | 20,511 | 194,166 | 156,309 | 1,252 | 21,196 |

| Component | 22 | 23[a] | 24 | 26 | 27 | 28 | 29 | 31 | 32 |
|---|---|---|---|---|---|---|---|---|---|
| HF | — | 747 | — | 749 | 216 | 35 | 3 | — | — |
| Ethane | — | — | — | — | — | — | — | — | — |
| Propylene | — | — | — | — | — | — | — | — | — |
| Propane | 23 | 13 | — | 151 | 11,983 | 1,901 | 178 | — | — |
| Isobutane | 213 | 166 | — | 1,443 | 111,150 | 17,639 | 1,646 | 55 | 7 |
| Butenes | — | — | — | — | — | — | — | — | — |
| n-Butane | 13 | 7 | — | 87 | 7,023 | 1,115 | 104 | 1,097 | 394 |
| Pentanes+ | 3 | 3 | — | 10 | 1,535 | 254 | 23 | 164 | 21,078 |
| Total | 252 | (see below) | (see below) | (see below) | 131,907 | 20,944 | 1,954 | 1,316 | 21,479 |
| Acid Sol Oils | | 34 | 17 | 17 | | | | | |
| Water | | 16 | — | 16 | | | | | |
| Total | | 986 | 17 | 2,473 | | | | | |

[a]includes pump flush, not shown.

In operation, it will be seen from an overall viewpoint that tower 50 is charged continuously with alkylation hydrocarbon effluent 17 and tower 50 fractionates this preheated stream 17 into an overhead propane-containing vapor, a side-draw of isobutane vapor 18, a side-draw of normal butane vapor 31, and a liquid bottoms alkylate gasoline product 32. Tower 50 must have additional heat added thereto as by the reboiler located in the bottom thereof. This amount of additional heat required is sufficient to produce from stream 17, the alkylate 32, containing only that amount of normal butane desired therein, the normal butane vapor 31, the isobutane vapor 18, and the propane-containing overhead.

The top zone of tower 50, at the temperature sensing locus, is operated at a set temperature which allows the propane overhead, at the fixed reflux thereto, to have only a preselected amount of isobutane therein. The total propane ultimately removed from the system, from a depropanizer-HF stripper system, not shown, is equal to that propane introduced into the operation, e.g., by olefins 16, by depropanizer bottoms 37 and by feed 11, less any propane removed at 12 and 14, plus that amount of propane produced in the alkylation process 25.

The amount of heat added to the tower 50 reboiler can vary depending upon the composition (and quantity) of tower feed 17. If additional heat is required to boil up more isobutane, normal butane, and propane, at the constant reflux, then more isobutane vapor is removed at 18 in response to a tendency for the top tower temperature to increase. This tower top temperature is kept at a preset constant value, as stated and is related to the overhead composition desired by then increasing the flow of isobutane vapor 18 through condenser 45 and ultimately increasing the amount of isobutane vapor charged via 27 to the reboiler 35 on tower 10. As the amount of isobutane vapor 27 charged to reboiler 35 increases, the amount of isobutane vapor charged via 29 to condenser 45 decreases to a preset minimum quantity.

Tower 10 has two reboilers thereon. Reboiler 35 utilizes heat which is present in the isobutane vapor 27 which must be cooled and condensed before it is recycled to alkylation 25, and reboiler 33 which uses "outside heat" in the form of steam. It is the operation of the invention to maximize the use of the available heat in isobutane vapor 27 to add heat to tower 10, and to minimize the requirement for steam at 34. Also, it is the operation of the invention to minimize the amount of isobutane vapor passed to cooler-condenser 45.

Feed 11 to tower 10 comprises isobutane and normal butane. Isobutane is taken overhead via 13 for change to alkylation 25. Normal butane is removed at 12. A side-draw 14 is taken off with no more than about 10 percent isobutane therein, for example, by removing stream 14 at this preselected isobutane percentage therein, normal butane 12 has a preselected minimum amount of isobutane removed therewith, as desired.

When the analysis at 14 shows a tendency for an increase in isobutane therein, e.g., an increased trend in isobutane is detected, this means that more heat is needed in the bottom of tower 10 to drive isobutane up the column. When isobutane 27 is at its maximum flow through reboiler 35, for example, then this additional heat needed in the bottom of 10 is added via reboiler 33, using additional steam 34. When the isobutane in 14 tends to decrease below a preselected percent, then, conversely, less reboil of tower 10 is needed, and at maximum isobutane 27 flow, the flow of steam 34 through reboiler 33 is decreased, boiling up tower 10 less isobutane, so that the preselected percent is maintained in 14, e.g., at the above 10 percent, given by way of example.

Reasonable variation and modification are possible with the scope of the foregoing disclosure, the drawing, and the appended claims to the invention the essence of which is that an operating condition in a fractionation is at least in part controlled by withdrawing from said fractionation a heat-containing fluid at a rate responsive to and correlated with a detected change in said condition and utilizing the heat in the withdrawn fluid as in the overall operation; that by controlling an alkylation product fractionator top portion temperature by removing, responsive to tendency of said temperature to change, more or less hot isobutane vapor from said fractionator, as described, the total flow of hot isobutane vapor to a reboiler furnishing a portion of the heat to a mixed butanes fractionator can be maximized, also as described, thus minimizing the portion remaining of heat needed to reboil said reboiled fractionator furnished as by steam, also as described.

I claim:

1. In an operating unit in which there is a first fractionator being reboiled with a steam reboiler and with a stream of heat-containing fluid taken from a second fractionator and passed into and through a second reboiler in said first fractionator, wherein said second reboiler is being supplied with said fluid separated from said second fractionator having a locus in a top portion thereof and wherein a maximum use of said fluid to said second reboiler and a minimum use of steam to said steam reboiler are to be provided, the invention which comprises: detecting a change in a controlled variable at said locus in said top portion of said second fractionator and adjusting the rate of flow of said fluid from said second fractionator to said second reboiler to return said controlled variable to the condition desired in said top portion of said second fractionator.

2. An operation according to claim 1 wherein said fluid is a vapor.

3. An operation according to claim 1 wherein said fluid is a liquid.

4. The operation of claim 1 wherein the condition desired for a said locus is temperature.

5. The operation of claim 1 wherein the condition desired for a said locus is pressure.

6. The operation according to claim 1 wherein the condition desired for said locus is composition.

7. The operation of claim 1 wherein the condition desired for said locus is at least one of temperature, pressure and composition.

8. In an operating unit in which there is a mixed butane feed fractionater being separately reboiled with a steam reboiler and a hot isobutane vapor reboiler wherein said hot isobutane vapor reboiler is being supplied with hot isobutane vapor separated from an alkylate product fractionator having a locus in a top portion thereof and wherein a maximum use of said hot isobutane vapor to said hot isobutane vapor reboiler and a minimum use of steam to said steam reboiler are to be provided, the invention which comprises: detecting a change in a controlled variable at said locus in said top portion of said alkylate product fractionator and adjusting the rate of flow of hot isobutane vapor from said alkylate product fractionator to said hot isobutane reboiler to return said controlled variable to the condition desired in said top portion of said alkylate product fractionator.

9. An operation according to claim 8 wherein the effect of the variation in the flow rate of hot isobutane vapor passed through said reboiler is detected and the amount of any steam necessary to maintain desired conditions in the mixed butane fractionator is adjusted accordingly.

10. The operation of claim 8 wherein the heat requirement for the mixed butanes feed fractionator is supplied by the flow of hot isobutane to its hot isobutane reboiler and the amount of steam added to its steam reboiler is adjusted to supply the balance of the total heat requirement to the mixed butane feed fractionator.

11. The operation of claim 10 wherein a first condition in a locus of the mixed butane feed fractionator is determined, said first condition is compared with a second condition desired for said locus of said mixed butane feed fractionator and addition of steam to said steam reboiler is adjusted accordingly.

12. The operation of claim 10 wherein the condition desired for said locus is temperature.

13. The operation of claim 10 wherein the condition desired for said locus is pressure.

14. The operation according to claim 10 wherein the condition desired for said locus is composition.

15. The operation of claim 10 wherein the condition desired for said locus is at least one of temperature, pressure and composition.

16. In an operating unit in which there is a mixed paraffin feed fractionator being separately reboiled with a steam reboiler and a hot isoparaffin vapor reboiler wherein said hot isoparaffin vapor reboiler is being supplied with hot isoparaffin vapor separated from an alkylate product fractionator having a locus in a top portion thereof and wherein a maximum use of said hot isoparaffin vapor to said hot isoparaffin vapor reboiler and a minimum use of steam to said steam reboiler are to be provided, the invention which comprises: detecting a change in a controlled variable at said locus in said top portion of said alkylate product fractionator and adjusting the rate of flow of hot isoparaffin vapor from said alkylate product fractionator to said hot isoparaffin reboiler to return said controlled variable to the condition desired in said top portion of said alkylate product fractionator.

17. The operation of claim 16 wherein a first condition in a locus of the mixed paraffin feed fractionator is determined, said first condition is compared with a second condition desired for said locus of said mixed butane feed fractionator and addition of steam to said steam reboiler is adjusted accordingly.

* * * * *